United States Patent [19]

Listemann et al.

[11] Patent Number: 5,144,074
[45] Date of Patent: Sep. 1, 1992

[54] PROCESS FOR THE SYNTHESIS OF CARBOXAMIDES

[75] Inventors: Mark L. Listemann, Whitehall; Ronald Pierantozzi; John N. Armor, both of Orefield, all of Pa.

[73] Assignee: Air Products and Chemicals, Inc., Allentown, Pa.

[21] Appl. No.: 159,807

[22] Filed: Feb. 24, 1988

[51] Int. Cl.$^5$ .................. C07C 231/12; C07C 233/18
[52] U.S. Cl. ..................................... 564/224; 564/219
[58] Field of Search ................ 564/185, 186, 219, 224

[56] References Cited

U.S. PATENT DOCUMENTS

| | | | |
|---|---|---|---|
| 4,018,826 | 4/1977 | Gless, Jr. et al. | 260/583 P |
| 4,322,271 | 3/1982 | Jensen et al. | 204/73 R |
| 4,334,097 | 6/1982 | Schmidt | 564/201 |
| 4,544,377 | 11/1985 | Stackman et al. | 564/205 |
| 4,567,300 | 1/1986 | Murao et al. | 564/215 |

FOREIGN PATENT DOCUMENTS 1273533 7/1968 Fed. Rep. of Germany .

OTHER PUBLICATIONS

R. W. Stackman and Richard H. Summerville, Ind. Eng. Chem. Prod. Des. Div. 1985, 24, 242–246, "Synthesis of N-Vinylacetamide and Preparation of Some Polymers and Copolymers".

*Primary Examiner*—Carolyn Elmore
*Attorney, Agent, or Firm*—Russell L. Brewer; James C. Simmons; William F. Marsh

[57] ABSTRACT

Carboxamides having the structural formula:

$$R^1CHR^2CH(OR^3)NHCR^4O$$

wherein:
$R^1$ is H, $C_1$–$C_6$ alkyl or aryl;
$R^2$ is H, $C_1$–$C_6$ alkyl;
$R^3$ is benzyl, $C_1$–$C_8$ alkyl or hydroxyalkyl; and
$R^4$ is H, $C_1$–$C_6$ alkyl or aryl;

are synthesized by reacting an aldehyde having the structural formula: $R^1CHR^2CHO$ wherein $R^1$ and $R^2$ are as defined above, with an alcohol having the structural formula: $R^3OH$, wherein $R^3$ is as defined above, and an amide having the structural formula: $R^4CONH_2$ wherein $R^4$ is as defined above, in the presence of a strong acid catalyst at a temperature in the range of 0°–200° C.

14 Claims, No Drawings

PROCESS FOR THE SYNTHESIS OF CARBOXAMIDES

TECHNICAL FIELD OF THE INVENTION

The present invention relates to the synthesis of various carboxamide compounds.

BACKGROUND OF THE INVENTION

Secondary N-vinyl carboxylic acid amides can be polymerized to give water-soluble homopolymers and copolymers. Such polymerizations are disclosed in Gless, et al., U.S. Pat. No. 4,018,826. The N-vinyl carboxylic acid amides used in the polymerization can be obtained by removing an alcohol from N-(1-alkoxyethyl)carboxylic acid amides. Jensen, et al., U.S. Pat. No. 4,322,271 discloses a three-stage process for forming N-vinyl-N-alkyl-carboxylic acid amides starting from N-ethyl-carboxylic acid amides. The N-ethyl-carboxylic acid amides undergo anodic alkoxylation to form N-$\alpha$-alkoxyethyl-carboxylic acid amides which are subsequently heated to split off an alcohol and form the final product. Stackman, et al. U.S. Pat. No. 4,554,377 discloses a process for preparing N-$\alpha$-alkoxyethyl-carboxylic acid amides from dimethyl acetal and a carboxylic acid amide, and subsequently for the synthesis of secondary N-vinyl carboxylic acid amides therefrom.

While the above-described methods have been applied for forming secondary N-vinyl carboxylic acid amides, existing methods for the preparation of the starting materials; i.e., N-(1-alkoxyethyl) carboxylic acid amides are inefficient and impractical when applied on an industrial scale. Such methods for forming N-(1-alkoxyethyl) carboxylic acid amides include the electrochemical alkoxylation of N-ethyl carboxylic acid amides with alcohols. While the electrochemical processes do operate cleanly and in good yields, the operations are complex and recovery of the conducting salts is expensive.

Schmidt, U.S. Pat. No. 4,334,097 discloses a process for preparing N-$\alpha$-alkoxylalkyl-carboxamides by reacting primary or secondary amides of aliphatic, araliphatic or aromatic carboxylic acids or cyclic carboxamides which are not capable of forming an aromatic system, with open-chain $\alpha$ halogenoalkyl ethers in the presence of tertiary amines. This process, however, requires the disposal of large quantities of acid salts.

Primary alkyl carboxylic acid amides react with acetaldehyde dimethyl acetal to give N-(1-methoxyethyl) carboxylic acid amides. This process requires large excesses of acetal; i.e., about 20:1; to achieve practical yields and purities, and is reported to fail for formamide. See R. W. Stackman, et al., *Ind. Eng. Chem. Prod. Res. Dev.* (1985), 24, 242–246.

Murao, et al., U.S. Pat. No. 4,567,300 and Great Britain equivalent 2 152 929 A discloses a process wherein acetaldehyde reacts with formamide in the presence of a weakly basic catalyst to yield solid N-(1-hydroxyethyl) formamide which, following catalyst neutralization, reacts with alcohols in the presence of an acid catalysts to yield N-(1-alkoxyethyl) formamide. This process is unattractive in that it requires two discrete steps, the handling of a solid intermediate, and the disposal of salts.

H. Bestian, et al., German Patent 1,273,533, discloses the synthesis of tertiary N-(1-alkoxyethyl) carboxylic acid amides from the reaction of acetaldehyde, alcohol, and secondary amide at 50°–150° C. using a 1.5–4 molar excess of acetaldehyde vs. amide.

BRIEF SUMMARY OF THE INVENTION

The present invention is a process for synthesizing carboxamides having the structural formula:

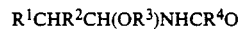

wherein:
$R^1$ is H, $C_1$–$C_6$ alkyl or aryl;
$R^2$ is H, or $C_1$–$C_6$ alkyl;
$R^3$ is benzyl, $C_1$–$C_8$ alkyl or hydroxyalkyl; and
$R^4$ is H, $C_1$–$C_6$ alkyl or aryl;

The process comprises reacting an aldehyde having the structural formula: $R^1CHR^2CHO$ wherein $R^1$ are $R^2$ are as defined above, with an alcohol having the structural formula: $R^3OH$, wherein $R^3$ is as defined above, and an amide having the structural formula: $R^4CONH_2$ wherein $R^4$ is as defined above, in the presence of a strong acid catalyst at a temperature in the range of 0°–200° C.

In this process, the rapid, acid catalyst reaction of an alcohol with an aldehyde and an amide to form the above-described carboxamide product is carried out in a single step. Unlike prior processes, the isolation and handling of solid intermediates and the disposal of salts are not required with this process. Additionally, any acetal produced, and not subsequently consumed, can be recycled and mixed directly with the feedstock.

DETAILED DESCRIPTION OF THE INVENTION

Carboxamides having the structural formula:

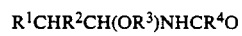

wherein:
$R^1$ is H, $C_1$–$C_6$ alkyl or aryl; $R^2$ is H, $C_1$–$C_6$ alkyl; $R^3$ is benzyl, $C_1$–$C_8$ alkyl or hydroxyalkyl; and $R^4$ is H, $C_1$–$C_6$ alkyl or aryl are synthesized by the single step reaction of an aldehyde and alcohol with an amide in the presence of a strong acid catalyst. Aldehydes suitable for this reaction are any which have the structural formula $R^1CHR^2CHO$ wherein $R^1$ and $R^2$ are as defined above, and any alcohol having the formula $R^3OH$ wherein $R^3$ is as defined above with ethanol generally being preferred and any amide having the structural formula $R^4CONH_2$ wherein $R^4$ is as defined above can be used. Additionally, other alcohols, such as functional alcohols (e.g. fluorinated) can be used without adversely effecting the reaction.

It has been found that the acid catalyzed reaction of an alcohol with an aldehyde and an amide to form the above-described product can be carried out without the necessity of handling solids and without forming salts. Additionally, any acetal present in the resultant product mixture can be recycled directly to the feedstock mixture.

The reaction is carried out in the presence of a strong acid catalyst, of which preferred examples include the macroreticular anhydrous sulfonic acid resin Amberlyst 15, XN-1010 both available commercially from Rohm & Haas, and $CH_3SO_3H$. Optionally, the aldehyde and alcohol may be contacted with a weak base catalyst before adding the amide and acid catalyst, or the reaction may be run in the presence of a mixture of strong acid and weak base catalyst. Base catalyst is not necessary, however, and the preferred method is to use only a strong acid catalyst.

When carrying out the reaction, the reactants may be added together, or in any order with the proviso that the formamide and alcohol should not be mixed with the catalyst prior to adding the aldehyde since they would react to form unwanted alkylformates. For best results, the reactants should be added in an alcohol:amide ratio of 1:1 to 5:1 and preferably in an aldehyde:alcohol:amide molar ratio of about 1:1-2:1 with a catalyst loading of at least 0.1 mole %, and preferably for formamide between about 16-20 mole % $H^+$ vs. amide. Higher amounts of acid were shown to be not beneficial, while lower amounts result in lower product yield. The reaction is run at a temperature from about 0°–200° C., with a preferred range being from 20°–60° C. for a time ranging from about 0.25–24 h, and preferably from 2–4 h, and typically at atmospheric or autogeneous pressure.

The reaction is best run undiluted, as the presence of a solvent, while not detrimental to selectivities, tends to lower conversions. Even small amounts of water; e.g., 0.2 mole per mole $H_2NCHO$, lowers product yields. Additionally, hydrated strong acid resins are generally less effective catalysts for the reaction than anhydrous resins.

The present process is advantageous over the prior art methods, such as Murao, U.S. Pat. No. 4,567,300, in that it is operated in a single step, free of solids handling and salt disposal. The process is characterized as "single step" in that all the reactants are initially mixed to form the final product without the necessity of isolating intermediates, adding other reactants, or interrupting the reaction prior to final product formation. Additionally, contrary to the teachings of R. H. Summerville, et al. *Polymer Preprints* (1983) 24, 12-13, it has now been demonstrated that formamide can be used in this type of process to yield the desired products.

The following examples were carried out to further illustrate the present invention and are not meant to be limiting.

EXAMPLE 1

The process of the present invention was carried out to produce N-(1-ethoxyethyl)formamide (EEF) by reacting acetaldehyde with ethanol and formamide in a molar ratio of 1:1.5:1, respectively. The reaction was catalyzed using 0.18 mole eq. (based on formamide) of the strong acid catalyst XN-1010. The reaction was run, undiluted, for 4 h at about 25° C., after which the product was collected and analyzed. The yields and mass balance for this reaction are reported in Table 1 below.

TABLE 1

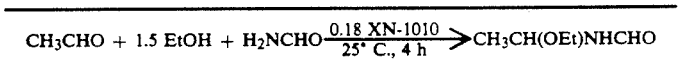

$CH_3CHO + 1.5\ EtOH + H_2NCHO \xrightarrow[25°\ C.,\ 4\ h]{0.18\ XN-1010} CH_3CH(OEt)NHCHO$

| | | | % Yields | | | |
|---|---|---|---|---|---|---|
| EEF | Bis | HCOOEt | $H_2NCHO$ | $CH_3CH(OEt)_2$ | EtOH | $CH_3CHO$ |
| 58 | <1 | 9 | 13 | 8 | 63 | 12 |

% Conv. $H_2NCHO$ = 87, % Conv. $CH_3CHO$ = 66
% Selectivities: EEF (67), Bis (<1), HCOOEt (10), HCOOH (~10) (vs. $H_2NCHO$)
% Selectivities: EEF (88), Bis (<1), $CH_3CH(OEt)_2$ (12) (vs. $CH_3CHO$)
With acetal recycle - total acetaldehyde based selectivity is 99% to EEF.

From the results reported in Table 1 above, it can be seen that the reaction produced high yields of EEF, at high selectivities; i.e., low yields of undesirable ethylidene-bis-formamide (Bis).

EXAMPLE 2

The reaction of Example 1 was carried out using an acetaldehyde:ethanol:formamide ratio of 1:2:1 over various catalyst combinations. The specific catalyst combinations, as well as the results of each run are reported in Table 2 below.

TABLE 2

Acid-Base Catalyst Combinations

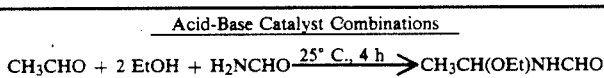

$CH_3CHO + 2\ EtOH + H_2NCHO \xrightarrow{25°\ C.,\ 4\ h} CH_3CH(OEt)NHCHO$

| Catalyst(a) Combination | % Yields(b) | | | | | |
|---|---|---|---|---|---|---|
| | EEF | Bis | HCOOEt | $H_2NCHO$ | $CH_3CH(OEt)_2$ | EtOH |
| 1 | 54 | <1 | 7 | 22 | 19 | 93 |
| | 59 | <1 | 7 | 14 | 20 | 96 |
| 2 | 53 | <1 | 6 | 27 | 17 | 80 |
| 3 | 62 | <1 | 13 | 15 | 14 | 94 |
| | 58 | <1 | 11 | 10 | 21 | 103 |
| 4 | 52 | <1 | 10 | 14 | 15 | 90 |
| 5 | 37 | <1 | 6 | 14 | 7 | 53 |

(a)Combination 1: 0.098 A-21 and 0.18 XN-1010 (mole % v. formamide in all cases) combined in reaction vessel, followed by formamide and acetaldehyde/ethanol mixture.
Combination 2: Acetaldehyde/ethanol stirred over 0.098 A-21 for 1 hour followed by addition of formamide and 0.18 XN-1010.
Combination 3: Acetaldehyde/ethanol stirred over 0.049 A-21 for 1 hour, hemiacetal solutions syringed into vessel containing formamide and 0.18 XN-1010.
Combination 4: Acetaldehyde/ethanol added to formamide and 0.18 XN-1010.
Combination 5: Acetaldehyde: 1.5 EtOH: $H_2NCHO$ stirred over 0.05 A-21 1 hour, then transferred to 0.18 XN-1010 for 4 hours.
(b)All % yields based on formamide.

The results reported in Table 2 clearly indicate that the present reaction produces high yields of EEF product when a strong acid/weak base catalyst system is used. In all instances the formation of unwanted by-product (Bis) was extremely small.

EXAMPLE 3

Several runs were carried out to determine the effect of temperature on the reaction set out in Example 1. Specific reaction conditions and catalyst combinations for each of the runs, along with the product distributions are set out in Table 3 below.

TABLE 3

Effect of Temperature $$CH_3CHO + 2\ EtOH + H_2NCHO \xrightarrow{4\ h} CH_3CH(OEt)NHCHO$$

| Catalyst[a] Combination | Temp (°C.) | Time (h) | % Yields[b] | | | | | |
|---|---|---|---|---|---|---|---|---|
| | | | EEF | Bis | HCOOEt | $H_2NCHO$ | $CH_3CH(OEt)_2$ | EtOH |
| 1 | 25 | 4 | 54 | <1 | 7 | 22 | 19 | 93 |
| " | 25 | 4 | 59 | <1 | 7 | 14 | 20 | 96 |
| " | 40 | 4 | 56 | 6 | 7 | 10 | 17 | 89 |
| " | 60 | 4 | 47 | 10 | 9 | 17 | 14 | 92 |
| 3 | 25 | 4 | 58 | <1 | 11 | 10 | 21 | 103 |
| " | 40 | 4 | 50 | <1 | 11 | 15 | 18 | 93 |
| " | 60 | 4 | 48 | 7 | 11 | 20 | 16 | 95 |
| 4 | 25 | 4 | 52 | <1 | 10 | 14 | 15 | 90 |
| " | 40 | 4 | 51 | <1 | 12 | 20 | 14 | 101 |
| " | 60 | 4 | 50 | <1 | 14 | 23 | 14 | 99 |

[a]See Footnote (a), Table 1.
[b]All % yields based on formamide.

High product (EEF) yields were observed for all runs in the temperature range tested above; i.e., 25°-60° C. The Bis yields remained low, although for two of the catalyst combinations, 1 and 3, the yields did show an increase at higher temperatures.

EXAMPLE 4

The reaction of Example 1 above was carried out for several runs to determine the effect various ethanol-:acetaldehyde ratios had on product distribution. The reactions were carried out for four hours at 25° C. over a strong acid (0.18 XN-1010), weak base (0.09 A-21) catalyst combination. The specific ratios, along with the product yields are set out in Table 4 below.

TABLE 4

Variation of the Ethanol to Acetaldehyde Ratio $$CH_3CHO + X\ EtOH + H_2NCHO \xrightarrow[0.18\ XN\text{-}1010,\ 4\ h]{0.098A\text{-}21,\ 25°\ C.^{(a)}} CH_3CH(OEt)NHCHO$$

| Ethanol:Acetaldehyde Ratio (x) | % Yields[b] | | | | | |
|---|---|---|---|---|---|---|
| | EEF | Bis | HCOOEt | $H_2NCHO$ | $CH_3CH(OEt)_2$ | EtOH |
| 1.2[c] | 55 | 8 | 5 | 19 | 10 | 51 |
| 1.5 | 54 | <1 | 4 | 10 | 10 | 57 |
| 2.0 | 54 | <1 | 7 | 22 | 19 | 93 |
| 3.0 | 36 | <1 | 10 | 34 | 41 | 172 |

[a]In all cased formamide added to the acid/base resin mixture, followed by the acetaldehyde/ethanol mixture. Reactions stirred 4 hours at 25° C.
[b]All % yields are based on formamide.
[c]Diluted with 1.3 g triglyme and 1.0 g THF to improve stirring.

The data reported above show high EEF yields at ethanol:acetaldehyde ratios ranging from 1.2–2.0, with the yield decreasing at a ratio of 3.0.

EXAMPLE 5

The reaction of Example 1 above was carried out for several runs to determine the effect various acetaldehyde:ethanol:formamide ratios had on product distribution. The runs were carried out for four hours at 25° C. over a strong acid catalyst (XN-1010). The specific ratios along with the product yields for these runs are set out in Table 5 below.

TABLE 5

Variation of the Acetaldehyde:Ethanol:Formamide Ratio $$x\ CH_3CHO + y\ EtOH + z\ H_2NCHO \xrightarrow[25°\ C.,\ 4\ h]{0.18\ XN\text{-}1010} CH_3CH(OEt)NHCHO$$

| Ratios[a] | | | % Yields[b] | | | | | |
|---|---|---|---|---|---|---|---|---|
| x, | y, | z | EEF | Bis | HCOOEt | $H_2NCHO$ | $CH_3CH(OEt)_2$ | EtOH |
| 1 | 1.5, | 1 | 58 | <1 | 9 | 13 | 8 | 63 |
| 2, | 3, | 1 | 60 | <1 | 8 | <1 | 38 | 127 |
| 1.5, | 1.5, | 1 | 44 | <1 | 5 | <1 | 9 | 57 |
| 1, | 1.33 | 1.33 | 60 | 2 | 4 | 26 | 3 | 53 |

[a]Ratios x and y are mole equivalents relative to formamide.
[b]All % yields based on formamide.

The data reported above show high EEF yields were achieved for all the runs, although the run wherein both the acetaldehyde and alcohol were increased (e.g. to 2 and 3, respectively), more acetal had to be recycled.

EXAMPLE 6

Several runs were carried out for the reaction of Example 1 to determine the effect of reaction time on product (EEF) yield. Specific reaction conditions, along with the results are set out in Table 6 below.

TABLE 6

Reaction Time $$CH_3CHO + 1.5\ EtOH + H_2NCHO \xrightarrow[25^\circ C.,]{0.18\ XN\text{-}1010} CH_3CH(OEt)NHCHO$$

| Time (h) | % Yields[a] | | | | | |
|---|---|---|---|---|---|---|
| | EEF | Bis | HCOOEt | H₂NCHO | CH₃CH(OEt)₂ | EtOH |
| 0.25 | 27 | <1 | <1 | 61 | 19 | 65 |
| 0.5 | 37 | <1 | 3 | 52 | 13 | 70 |
| 1 | 45 | 1 | 4 | 31 | 13 | 54 |
| 2 | 50 | <1 | 5 | 19 | 9 | 62 |
| 4 | 58 | <1 | 9 | 13 | 8 | 63 |
| 6 | 58 | <1 | 8 | 13 | 6 | 63 |

[a]All % yields based on formamide.

The above results indicated that, for these particular runs, good yields are obtained after only 0.25 h, and the yield more than doubled at 4 h, and showed no further charge at 6 h.

EXAMPLE 7

Runs were carried out to determine the effect of catalyst loading on the reaction of Example 1. The specific reaction conditions, including the specific catalysts used for each run, along with the results are set out in Table 7 below.

TABLE 7

Catalyst Loading $$CH_3CHO + 1.5\ EtOH + H_2NCHO \xrightarrow[4\ h]{25^\circ C.} CH_3CH(OEt)NHCHO$$

| Catalyst[a] (mole eq.) | % Yields[b] | | | | | |
|---|---|---|---|---|---|---|
| | EEF | Bis | HCOOEt | H₂NCHO | CH₃CH(OEt)₂ | EtOH |
| XN-1010 (0.06) (1 h run) | 23 | <1 | <1 | 39 | 21 | 56 |
| XN-1010 (0.12) | 50 | <1 | 4 | 18 | 9 | 61 |
| XN-1010 (0.18) | 58 | <1 | 9 | 13 | 8 | 63 |
| XN-1010 (0.24) | 58 | <1 | 12 | 10 | 7 | 54 |
| 0.50 XN-1010 (+2 Et₂O) | 37 | <1 | 21 | <1 | 13 | 55 |
| 0.18 XN-1010[c] 0.06 XN-1010 | 56 | 2 | 9 | 18 | 7 | 52 |
| Amberlyst 15 (0.18) | 55 | 9 | 8 | 11 | 6 | 57 |
| Amberlyst 15 (0.24) | 50 | 9 | 17 | 21 | 10 | 53 |
| Amberlyst 15/ H₂O (0.18) | 48 | <1 | 8 | 23 | 5 | 75 |
| Amberlyst 15/ H₂O (0.24) | 41 | <1 | 8 | 20 | 4 | 76 |

[a]Mole equivalents relative to formamide.
[b]All % yields based on formamide.
[c]Initially charged 0.18 XN-1010 and ran for 3 hours then added a fresh portion (0.06) of XN-1010 and ran for a further 3 hours.

From these results, it can be seen that all of the strong acid catalysts used resulted in high product yields, although the hydrated resins were slightly less effective than anhydrous resins.

EXAMPLE 8

Runs were carried out to determine the effect various catalysts; i.e., solid and homogeneous, had on product yield. The reaction conditions, catalysts, and results are reported in Table 8 below.

TABLE 8

Comparison of Solid and Homogeneous Acid $$CH_3CHO + 1.5\ EtOH + H_2NCHO \xrightarrow{25^\circ C., 4\ h} CH_3CH(OEt)NHCHO$$

| Catalyst[a] (mole eq.) | % Yields[b] | | | | | |
|---|---|---|---|---|---|---|
| | EEF | Bis | HCOOEt | H₂NCHO | CH₃CH(OEt)₂ | EtOH |
| XN-1010 (0.18) | 58 | <1 | 9 | 13 | 8 | 63 |
| XN-1010 (0.18) (60 mesh) | 56 | <1 | 8 | 14 | 6 | 70 |
| Amberlyst 15 (0.18) | 55 | 9 | 8 | 11 | 6 | 57 |
| Wet Amberlyst 15 (0.18) | 48 | <1 | 8 | 23 | 5 | 75 |
| K-10[c] | <1 | <1 | <1 | 77 | 33 | 63 |
| XN-1010 + HCOOH (0.18 each) | 56 | 2 | 19 | 13 | 6 | 53 |
| HCOOH | <1 | <1 | <1 | 62 | 17 | 141 |

TABLE 8-continued

Comparison of Solid and Homogeneous Acid

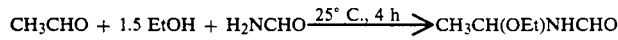
CH$_3$CHO + 1.5 EtOH + H$_2$NCHO $\xrightarrow{25° C., 4 h}$ CH$_3$CH(OEt)NHCHO

| Catalyst[a] (mole eq.) | % Yields[b] | | | | | |
|---|---|---|---|---|---|---|
| | EEF | Bis | HCOOEt | H$_2$NCHO | CH$_3$CH(OEt)$_2$ | EtOH |
| (0.18) HCOOH | <1 | <1 | <1 | 55 | 36 | 55 |
| (0.50) CH$_3$SO$_3$H | 42 | <1 | 15 | 23 | 23 | 87 |
| (0.18) FeCl$_3$ | 3 | <1 | <1 | 100 | 29 | 66 |
| (0.06) | | | | | | |

[a]Mole equivalents relative to formamide.
[b]All % yields based on formamide.
[c]K-10 montmorillonite clay. See Laszlo, P. Science 235, 20 March 1987, 1473-7.

From the results in Table 8 above, it can be seen that K-10 montmorillonite clay, HCOOH and FeCl$_3$ are poor catalysts for the present invention, whereas the strong acids, Amberlyst 15, XN-1010, and CH$_3$SO$_3$H work extremely well. Additionally, XN-1010 showed good results in either particle or mesh size.

EXAMPLE 9

Runs were carried out to determine the effect of solvents on the reaction of the present invention. The reaction of Example 1 was run using various solvents and also undiluted for comparison. In all cases XN-1010 was the catalyst used. The reaction conditions and results are reported in Table 9 below.

TABLE 9

Effect of Solvents on Product Distribution

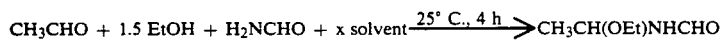
CH$_3$CHO + 1.5 EtOH + H$_2$NCHO + x solvent $\xrightarrow{25° C., 4 h}$ CH$_3$CH(OEt)NHCHO

| Solvent (mole eq.)[a] | % Yields[b] | | | | | |
|---|---|---|---|---|---|---|
| | EEF | Bis | HCOOEt | H$_2$NCHO | CH$_3$CH(OEt)$_2$ | EtOH |
| None | 58 | <1 | 9 | 13 | 8 | 63 |
| Hexane (2.0) | 41 | <1 | — | 12 | 23 | 42 |
| Et$_2$O (2.0) | 50 | <1 | 6 | 23 | 12 | 55 |
| THF (2.0) | 43 | <1 | 6 | 20 | 7 | 69 |
| H$_2$O (1.0) | 45 | <1 | 8 | 16 | 6 | 77 |
| H$_2$O (0.2) | 41 | <1 | 6 | 12 | 5 | 54 |
| NMP (1.0) | 45 | 2 | <1 | 46 | 13 | 68 |
| CH$_3$CN (2.0) | 58 | 2 | 8 | 22 | 8 | 55 |

[a]Mole equivalents relative to formamide.
[b]All % yields based on formamide.

As can be seen from the results reported in Table 9, the presence of a solvent generally has a detrimental effect on the reaction, with the exception that 2.0 mole eq. of CH$_3$CN showed no effect on EEF yield.

EXAMPLE 10

Runs were carried out to react acetaldehyde and alcohol with acetamide, in a molar ratio of 1:1.5:1 respectively. The reaction conditions and product yields are set out in Table 10 below.

TABLE 10

Reaction Using Acetamide

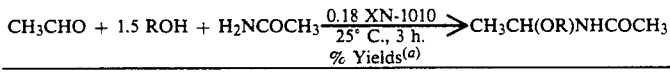
CH$_3$CHO + 1.5 ROH + H$_2$NCOCH$_3$ $\xrightarrow[25° C., 3 h.]{0.18\ XN\text{-}1010}$ CH$_3$CH(OR)NHCOCH$_3$

| ROH | % Yields[a] | | | | |
|---|---|---|---|---|---|
| | CH$_3$CH(OR)NHCOCH$_3$ | CH$_3$CH(NHCOCH$_3$)$_2$ | ROH | CH$_3$CH(OR)$_2$ | H$_2$NCOCH$_3$ |
| MeOH | ~30 | 19[b] | 67 | 25 | 16 |
| EtOH | ~35 | 20[b] | 83 | 12 | 15 |

[a]All % yields based on acetamide.
[b]Yields based on acetaldehyde equal ½ of those reported in the table.

From the results reported in Table 10, it can be seen that using acetamide as a reactant results in good product yields (CH$_3$CH(OR)NHCOCH$_3$), although somewhat less than the corresponding product yield when using formamide. Additionally, although relatively high levels of ethylidene bisacetamide (Bis) were produced, the levels were sufficiently low such that no precipitation of Bis was observed in either run.

Having thus described the present invention, what is now deemed appropriate for Letter Patent is set out in the following appended claims.

What is claimed is:

1. A process for the synthesis of carboxamides having the structural formula:

R$^1$CHR$^2$CH(OR$^3$)NHCHO wherein:
R$^1$ is H, C$_1$–C$_6$ alkyl or aryl;
R$^2$ is H, C$_1$–C$_6$ alkyl;
R$^3$ is benzyl, C$_1$–C$_8$ alkyl or hydroxyalkyl;

said process comprising reacting an aldehyde having the structural formula: $R^1CHR^2CHO$ wherein $R^1$ or $R^2$ are as defined above, with an alcohol having the structural formula: $R^3OH$, wherein $R^3$ is as defined above, and formamide having the structural formula $HCONH_2$ in an alcohol:formamide ratio of 1:1 to 5:1, in the presence of a strong acid catalyst present in a concentration of at least 6 mole % compared to formamide, at a temperature in the range of 0°–200° C.

2. A process in accordance with claim 1 wherein said reaction is carried out at autogeneous pressure.

3. A process in accordance with claim 1 wherein said temperature range is from 20°–60° C.

4. A process in accordance with claim 1 wherein said reaction is carried out for a period of time from 0.25 to 24 hours.

5. A process in accordance with claim 4 wherein said reaction is carried out for a period of time from 2 to 4 hours.

6. A process in accordance with claim 1 wherein the strong acid catalyst is macroreticular anhydrous sulfonic acid resin.

7. A process in accordance with claim 1 wherein the reactants are added in an aldehyde:alcohol:formamide ratio of about 1:1–2:1.

8. A process in accordance with claim 1 wherein acetaldehyde, ethanol and formamide are reacted to form secondary N-(1-ethoxyethyl)formamide.

9. A process in accordance with claim 1 wherein said strong acid catalyst also includes a weak base.

10. A process in accordance with claim 1 wherein the strong acid catalyst is present in a concentration range of 16–20 mol % of $H^+$ compared to formamide.

11. A process in accordance with claim 1 wherein said alcohol is ethanol.

12. A process in accordance with claim 1 wherein said aldehyde is acetaldehyde.

13. A process in accordance with claim 1 wherein acetal is formed during the reaction, and any acetal remaining with the product is recycled to the reaction feed.

14. A process in accordance with claim 8 wherein the reactants are added in an ethanol:formamide ratio of 1:1 to 2:1.

* * * * *